(12) United States Patent
Getalov

(10) Patent No.: US 8,894,269 B2
(45) Date of Patent: Nov. 25, 2014

(54) ULTRASONIC CAVITATION METHOD OF SIMULTANEOUS PROCESSING AND VOLUME PREPARATION OF EMULSION COSMETICS

(76) Inventor: Andrey Getalov, Moscow (RU)

( * ) Notice: Subject to any disclaimer, the term of this patent is extended or adjusted under 35 U.S.C. 154(b) by 0 days.

(21) Appl. No.: 13/882,979

(22) PCT Filed: Aug. 10, 2011

(86) PCT No.: PCT/RU2011/000601
§ 371 (c)(1),
(2), (4) Date: May 1, 2013

(87) PCT Pub. No.: WO2012/125067
PCT Pub. Date: Sep. 20, 2012

(65) Prior Publication Data
US 2013/0213484 A1 Aug. 22, 2013

(30) Foreign Application Priority Data
Mar. 16, 2011 (RU) .................................. 201109663

(51) Int. Cl.
*B01F 11/02* (2006.01)
*A61K 8/06* (2006.01)
*A61Q 19/00* (2006.01)
*B01F 3/08* (2006.01)

(52) U.S. Cl.
CPC . *A61K 8/062* (2013.01); *A61K 8/06* (2013.01); *A61Q 19/00* (2013.01); *B01F 11/0266* (2013.01); *B01F 3/0819* (2013.01); *A61K 2800/82* (2013.01)
USPC .......................................... 366/127; 366/144

(58) Field of Classification Search
CPC .. B01F 11/0275; B01F 11/0266; B01F 11/02; B01F 11/0283
USPC ........................... 366/127, 144–146, 114–115
See application file for complete search history.

(56) References Cited

U.S. PATENT DOCUMENTS

| 4,452,747 | A | 6/1984 | Gersonde |
| 7,622,510 | B2 * | 11/2009 | Arnaud ............................. 516/20 |
| 2009/0166177 | A1 | 7/2009 | Wenzel et al. |
| 2013/0203864 | A1 * | 8/2013 | Getalov ...................... 514/772.3 |
| 2013/0213484 | A1 * | 8/2013 | Getalov .............................. 137/3 |
| 2013/0215703 | A1 * | 8/2013 | Getalov et al. ................. 366/116 |
| 2013/0315025 | A1 * | 11/2013 | Getalov ......................... 366/108 |

FOREIGN PATENT DOCUMENTS

| EP | 279641 A2 * | 8/1988 | ............... A61K 7/00 |
| RU | 2173140 | 9/2001 | |
| RU | 2240782 | 11/2004 | |

(Continued)

*Primary Examiner* — Charles Cooley
(74) *Attorney, Agent, or Firm* — Lambert & Associates; Gary E. Lambert; David J. Connaughton, Jr.

(57) ABSTRACT

The invention relates to the field of cosmetology and for technology for obtaining cosmetic products for skin care. The method of simultaneous processing and obtaining cosmetic emulsion volumes involves placing the volume within the continuous-flow mechanical oscillation system where the resonant acoustic cavitation behavior is implemented, so that the acoustic wave from the wall of the channel falls perpendicular to the major edge of volume, and the material they are made of has a specific acoustic impedance being equal or close to the impedance of the liquid filling the channel system. The amplitude of the ultrasonic resonance oscillations exceeds the threshold of acoustic cavitation for the mixture of ingredients that are currently being processed.

14 Claims, 2 Drawing Sheets

(56) References Cited

FOREIGN PATENT DOCUMENTS

| RU | 2009119873 | 12/2010 |
| RU | 2419414 | 5/2011 |
| WO | 2012/150874 A1 * | 11/2012 |
| WO | 2013/015708 A1 * | 1/2013 |
| WO | 2013/032358 A1 * | 3/2013 |
| WO | 2013/176565 A1 * | 11/2013 |

* cited by examiner

```
┌─────────────────────────────────────────────────────────────────────────────────┐
│ Direct a flow of an oil phase and a water phase of a first cosmetics emulsion   │
│ through a rectangular tube, the rectangular tube being positioned within a flow │
│ chamber of a continuous flow mechanical oscillation chamber, the chamber        │
│ configured to provide ultrasonic cavitation to the first cosmetics emulsion.    │
└─────────────────────────────────────────────────────────────────────────────────┘
                                        ↓
┌─────────────────────────────────────────────────────────────────────────────────┐
│ Direct a flow of an oil phase and a water phase of a second cosmetics emulsion  │
│ through a rectangular tube, the rectangular tube being positioned within the    │
│ flow chamber of the continuous flow mechanical oscillation chamber configured   │
│ to provide ultrasonic cavitation to the second cosmetics emulsion.              │
└─────────────────────────────────────────────────────────────────────────────────┘
                                        ↓
┌─────────────────────────────────────────────────────────────────────────────────┐
│ Select a fluid for filling the flow channel to have a specific acoustic         │
│ impedance close to an acoustic impedance of the first and second emulsions.     │
└─────────────────────────────────────────────────────────────────────────────────┘
                                        ↓
┌─────────────────────────────────────────────────────────────────────────────────┐
│ Fill the flow channel with the fluid, the fluid filling around the first and    │
│ second rectangular tubes placed within the flow channel.                        │
└─────────────────────────────────────────────────────────────────────────────────┘
                                        ↓
                      ┌───────────────────────────────────┐
                      │ Control a temperature of the fluid.│
                      └───────────────────────────────────┘
                                        ↓
┌─────────────────────────────────────────────────────────────────────────────────┐
│ Select a vibrational amplitude of a wall of the chamber defining the flow       │
│ channel to exceed a threshold of acoustic cavitation of the first cosmetics     │
│ emulsion and second cosmetics emulsion.                                         │
└─────────────────────────────────────────────────────────────────────────────────┘
                                        ↓
┌─────────────────────────────────────────────────────────────────────────────────┐
│ Arrange the first tube to have a flat face arranged parallel to the wall when   │
│ placed in the chamber.                                                          │
└─────────────────────────────────────────────────────────────────────────────────┘
                                        ↓
┌─────────────────────────────────────────────────────────────────────────────────┐
│ Arrange the second tube to have a flat face arranged parallel to the wall when  │
│ placed in the chamber.                                                          │
└─────────────────────────────────────────────────────────────────────────────────┘
                                        ↓
┌─────────────────────────────────────────────────────────────────────────────────┐
│ Vibrate the wall of the chamber at the selected vibrational amplitude for a     │
│ predetermined time period, forming a wave that propagates perpendicularly to    │
│ the flat face of the first tubes.                                               │
└─────────────────────────────────────────────────────────────────────────────────┘
```

ULTRASONIC CAVITATION METHOD OF SIMULTANEOUS PROCESSING AND VOLUME PREPARATION OF EMULSION COSMETICS

CROSS REFERENCE TO RELATED APPLICATION

This application is for entry into the U.S. National Phase under §371 for International Application No. PCT/RU2011/000601 having an international filing date of Aug. 10, 2011, and from which priority is claimed under all applicable sections of Title 35 of the United States Code including, but not limited to, Sections 120, 363 and 365(c), and which in turn claims priority to Russian National Application RU 2011109663 filed on Mar. 16, 2011.

BACKGROUND

1. Field of the Invention

The invention relates to the field of cosmetology and dermatology, and can be used in biology, pharmacy, cosmetics, veterinary and food industry, in particular in cosmetic science for the development of technologies for manufacturing cosmetic products for skin, hair and nails.

2. Description of Related Art

It is known that the penetration of biologically active substances into the deeper layers of the skin also depends on the size and homogeneity of the oil phase of a cosmetic cream, which includes vegetable and essential oils as well as a number of important extracts and other oil-soluble ingredients. As a rule, in the technology of the cream manufacturing the tendency has been for dividing the oil phase by droplets having the size as small as possible.

In this case, along with liposomes of emulsion, "oil in water" biologically active ingredients being dissolved in the oil phase of the emulsion and adsorbed at the interface can penetrate through the layers of the epidermis.

It is known the method of manufacturing of a cosmetic cream that includes the following process steps:
Weighing and melting of the raw materials;
Preparation of oil and aqueous phase;
Emulsification;
Cooling and perfuming;
Packing in the packing materials.

For the preparation of the aqueous phase the ingredients are heated up to 75-80 degrees (Celsius). To prepare the oil phase the ingredients are heated up to 80-85 degrees. Further, there is mixture of the fat and aqueous phases. Under certain conditions (temperature, pH environment, entry order) DNA and preservatives are added to a creamy mass.

The disadvantage of this method is the considerable power requirement of the technologies for the cream manufacturing and reducing of the bioactivity of its components while preparation of the product due to the fact that the process of the emulsion is made by heating up to 80-85° C., further there is homogenization of the two phases, which makes difficult the adding of components and additives that are critical to thermal decomposition (temperature up to 40-45° C.) and at the same time required for homogenization. It is required to take into consideration of optimum temperature at different stages of adding supplements and vitamin complexes provided continuation of the process of homogenization. In case it is required to obtain several volumes of different emulsion formulations, it calls for parallel operation of multiple sets of equipment that greatly complicates the production and increases the cost of the products.

It is known the method of obtaining a cosmetic product in the form of emulsion comprising a dispersion of soluble components, emulsifiers, and biologically active substances (having any origin), solid powdered ingredients (sorbents or abrasives) in a solvent at room temperature therewith the components are added simultaneously or sequentially through the separate directly in the insonation chamber of rotary cavitation machine where cavitation emulsification process is implemented, while passing through the insonation chamber of emulsion complex "Myna" (or any other) and an aqueous solution.

This method also does not take an opportunity for simultaneous processing and homogenization of cosmetic emulsions with different composition and ingredients that may require different processing time and their optimal temperatures.

The closest is in fact a method wherein an increase of amplitude of acoustic waves in the treated liquid medium is effected due to the resonance in-phase oscillations of each of the long sides of the rectangular channel cross sections and additional superposition of waves inside the channel, at that the intrinsic distance is equal to the small side of the channel and is multiple of quarter of an acoustic wave in the treated medium. This allows to focus the maximum power on resonating oscillation frequency of the large side of the channel and to obtain a standing acoustic wave of high intensity inside the channel.

The research carried out by the company "DERMANIKA" revealed that the fundamental dispersity mode while such treatment procedure can be ~500 nanometers, the emulsion practically does not contain the dispersion phase more than 1000 nanometers (1 micron), the emulsion contains 2-3 times less emulsifier than usual. At that, the rotary-pulsed homogenizers allow to obtain emulsions in which the size of the dispersion phase is just beginning from 1000 nanometers (1 micron) with a larger volume of emulsifier.

The research has been partially reported at the XIV International scientific-practical conference "Cosmetics and raw materials: safety and efficiency" in October 2009, where it was marked the second place and a diploma, there are publications in designated magazines.

In the circumstances there is an improvement of the quality of the product, in accordance with the criteria (threshold) of cavitation and the resonant behavior with maximum efficiency, there are secured better key figures on intensification of combined physical-chemical, hydromechanical, heat-exchanging and mass-exchanging processes in the processing medium and the obtained at the output minimum size and homogeneity of fat (oil) phase.

This technology is implemented on an industrial scale in the operating cosmetic production plant "CJSC EMANSI Laboratory." The first products manufactured by this technology, hand cream Anti Smell Smoke (for smokers, against the influence of nicotine and smoke to hand skin), took the whole cycle of certification tests (Sanitary and epidemiological inspection report No. 77.01.12.915.P.006156.02.10 of Feb. 3, 2010 and the Declaration of conformity, the results of which are also confirmed by independent testing of laboratory "Spectrum" with the corresponding protocol No. 19 dated Dec. 22, 2009.

However, this technology also does not take an opportunity for simultaneous treatment of several cosmetic emulsions with different composition and ingredients.

SUMMARY

A method of simultaneously producing two different cosmetics emulsions is provided. The method beings with combining an oil phase and a first water phase of a first cosmetics emulsion in a first vessel having a substantially rectangular cross section. Similarly, a second oil phase and second water phase of a second cosmetics emulsion are combined in a second vessel having a substantially rectangular cross section, the second cosmetics emulsion has a different composition from the first cosmetics emulsion. The first and second vessels are placed in a continuous flow mechanical oscillation chamber, which is configured to provide ultrasonic cavitation to the first and second cosmetics emulsions. The vessels are arranged such that each has a major edge that is parallel to a wall of the chamber. The chamber is at least partially filled with a fluid to conduct the oscillations. This fluid is selected to have an acoustic impedance equal or similar to the first and second emulsions. The temperature of this fluid may be controlled, thus controlling the temperature of the first and second emulsions. A vibrational amplitude of the wall is determined to exceed a threshold of acoustic cavitation of the first and second emulsions. Because of the arrangement of the vessels, when the wall of the chamber is vibrated, it propagates a wave through the fluid perpendicularly to the major edges of the first and second vessels.

In an alternative embodiment, instead of a substantially rectangular vessel, the two cosmetics emulsions may be held within a tube, the length of the tube arranged to be parallel with a wall of the chamber. In this embodiment, the fluid may be stationary, or may pass through the tube at a pre-determined flow rate.

BRIEF DESCRIPTION OF THE FIGURES

FIG. 2 provides a flow chart of another embodiment of the invention.

DETAILED DESCRIPTION

Figure 1:
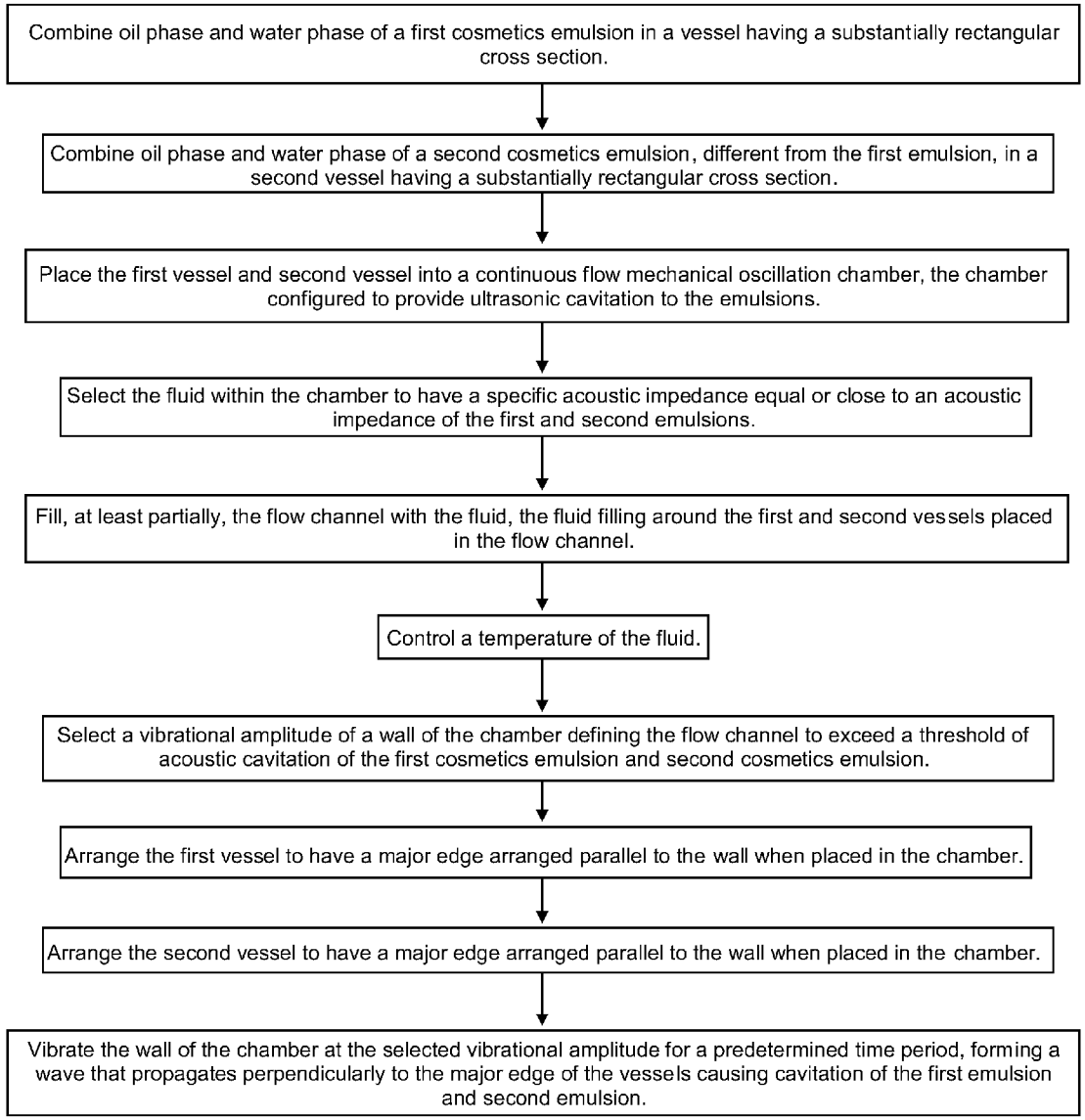
FIG. 1 provides a flow chart of an embodiment of the invention.

The aim of the invention is providing the possibility of simultaneous processing of multiple volumes of cosmetic emulsions with different composition of ingredients with provision of optimal temperature and processing time of each composition.

This aim is achieved by the fact that the volumes containing ingredients that have a rectangular profile, are involved in the channel system containing fluid so that the acoustic wave from the wall of the channel falls perpendicular to the major edge of volume. While the material from which they are made of has a specific acoustic impedance equal or close to the resistance of the liquid filling the channel system to the resistance of the treated mixture of cosmetics, the amplitude of ultrasonic resonance oscillations exceeds the threshold of acoustic cavitation for a mixture of ingredients that are currently being processed. Taking into account the loss while transmission through the walls of the volume and the optimum temperature of the mixture, the processing time is determined experimentally for obtaining the required stability of cosmetic emulsions.

The implementation of this method can be performed in two variants:

1. The rectangular cross-section channel system is dismountable and provides the possibility to organize the internal volumes as predominantly rectangular glasses, in which each glass-volume contains its particular composition of emulsion, and the interior volume of the channel system is fed or filled with the fluid through which the acoustic wave first hits on the wall of a glass-volume and then hits inside for creating a zone of fully-developed acoustic cavitation.

It is known that the reflectivity and transmission constant of an acoustic wave depend only on the wave resistance of the medium, and if the resistance is equal for the both media, for the normal incidence of a plane wave the above mediums are acoustically indistinguishable. There is no a boundary reflection, and the wave fully passes into the second medium, as if all volume was filled with only the first medium. For such a full penetration of the wave it is sufficient that the density and the acoustic velocity of both mediums are equal or close to each other, that is, the mechanical properties of the mediums must be congruent. It is sufficient to secure the equality or closeness of the products of the density and the acoustic velocity.

For example, if the fluid in the channel system is water, which can be a key component in the emulsion, it may be recommended to use the volumes being made of Teflon (velocity~1340 m/s, density of 1.76 g/cm3) or ebony (speed 2400 m/s, density of 1.15 g/cm3).

The wall thickness of the glass volume must be minimal to reduce losses during penetration of the acoustic wave.

2. The rectangular section channel system is pressure-proof and is within the range of volumes in the form of square tubes, which pumped work mediums. The larger parts of the channel system and volume-tubes are parallel to each other.

The acoustic impedances of fluid in the channel system, of the material of rectangular tube-volumes and of the processed mediums correspond to each other.

Thus, the simultaneous high intensity cavitation treatment of several emulsions is achieved.

At that, the operation principle of the channel system remains analogous to the prototype that takes an opportunity to obtain ultra-thin emulsions with the size of the dispersed phase up to 1000 nanometers.

Tuning of resonant vibrations of the walls of the channel system is effected in a like manner as in the prototype method. Specifically, after the theoretical calculation is carried out, for example, by the method, as a rule, it is required to take several actions for securing a more accurate tuning of resonant frequencies and obtaining the required Q characteristic.

The authors use their own method, which is based on the great number of material referred to instrumental measurements of the vibrational spectrum of rectangular channels. The next stage of the tuning is selection of the frequency of piezo-oscillator setting and their relative position in the rectangular cross section channel system (cassette). Accordingly, the frequency of piezo-oscillator must be adjusted close to the resonant frequency.

While arrangement of the emulsions several stages were determined:

Heating and mixing of water and oil phases at recommended temperatures (70-80 degrees Celsius);

Homogenization at 55-60° C. (optimum temperature for emulsifiers SE PF of COGNIS company);

Reduction of ultrasonic power and lowering the temperature to 47-48 degrees Celsius and putting active additives and flavorings;

Cosmetic emulsion homogenization means at the specified temperature;

Cooling and packing;

Homogenization of the oil and water phases at the specified temperature.

The treatment time was determined experimentally for obtaining a stable emulsion. The power of ultrasonic exposure was determined by the temperature of the treated mixture.

This method allows simultaneous obtainment of several different cosmetic emulsions, while maintaining the benefits that were in the prototype method. This method is effective for obtaining small amounts of cosmetic emulsions (from 30 ml), which leads to the mass production of cosmetic products for personal use, particularly for each specific customer at a significantly reduced costs.

The invention claimed is:

1. A method of simultaneously producing two different cosmetics emulsions comprising the steps of:
   combining a first oil phase and a first water phase of a first cosmetics emulsion in a first vessel, the first vessel having a substantially rectangular cross section;
   combining a second oil phase and second water phase of a second cosmetics emulsion in a second vessel, the second vessel having a substantially rectangular cross section, the second cosmetics emulsion having a different composition from the first cosmetics emulsion;
   placing the first vessel and second vessel into a continuous flow mechanical oscillation chamber, the chamber configured to provide ultrasonic cavitation to the first cosmetics emulsion and second cosmetics emulsion, the chamber defining a flow channel in which the first and second vessels are placed, and through which a fluid may flow;
   selecting the fluid to have a specific acoustic impedance equal or close to an acoustic impedance of the first and second emulsions;
   filling, at least partially, the flow channel with the fluid, the fluid filling around the first and second vessels placed in the flow channel;
   controlling a temperature of the fluid;
   selecting a vibrational amplitude of a wall of the chamber defining the flow channel to exceed a threshold of acoustic cavitation of the first cosmetics emulsion and second cosmetics emulsion;
   arranging the first vessel to have a major edge arranged parallel to the wall when placed in the chamber;
   arranging the second vessel to have a major edge arranged parallel to the wall when placed in the chamber; and
   vibrating the wall of the chamber at the selected vibrational amplitude for a predetermined time period, such that the vibrations form a wave that propegates perpendicularly to the major edge of the first vessel and the major edge of the second vessel, the vibrating causing cavitation of the first emulsion and second emulsion.

2. The method of claim 1 further comprising the step of flowing the fluid through the flow chamber.

3. The method of claim 1 further comprising the step of heating the first emulsion and second emulsion to approximately 70-80 degrees Celsius.

4. The method of claim 3 further comprising cooling the first emulsion and second emulsion to approximately 55-60 degrees Celsius during the step of vibrating the wall of the chamber.

5. The method of claim 4 further comprising the steps of reducing a power of the vibration of the wall;
   cooling the first emulsion and the second emulsion to approximately 47-48 degrees Celsius; and
   adding an additive or flavoring.

6. The method of claim 1 further comprising the step of transferring the vibration of the wall through the fluid, through the first vessel wall, and into the first cosmetics emulsion.

7. The method of claim 6 further comprising the step of transferring the vibration of the wall through the fluid, through the second vessel wall, and into the second cosmetics emulsion.

8. A method of simultaneously producing two different cosmetics emulsions comprising the steps of:
   directing a flow of a first oil phase and a first water phase of a first cosmetics emulsion through a first rectangular tube, the first rectangular tube being positioned within a flow chamber of a continuous flow mechanical oscillation chamber, the chamber configured to provide ultrasonic cavitation to the first cosmetics emulsion;
   directing a flow of a second oil phase and a second water phase of a second cosmetics emulsion through a second rectangular tube, the second rectangular tube being positioned within the flow chamber of the continuous flow mechanical oscillation chamber the chamber configured to provide ultrasonic cavitation to the second cosmetics emulsion;
   selecting a fluid for filling the flow channel to have a specific acoustic impedance close to an acoustic impedance of the first and second emulsions;
   filling the flow channel with the fluid, the fluid filling around the first and second rectangular tubes placed within the flow channel;
   controlling a temperature of the fluid;
   selecting a vibrational amplitude of a wall of the chamber defining the flow channel to exceed a threshold of acoustic cavitation of the first cosmetics emulsion and second cosmetics emulsion;
   arranging the first tube to have a flat face arranged parallel to the wall when placed in the chamber;
   arranging the second tube to have a flat face arranged parallel to the wall when placed in the chamber; and
   vibrating the wall of the chamber at the selected vibrational amplitude for a predetermined time period, such that the vibrations form a wave that propegates perpendicularly to the flat face of the first tube and the flat face of the second tube.

9. The method of claim 8 further comprising the step of flowing the fluid through the flow chamber.

10. The method of claim 8 further comprising the step of heating the first emulsion and second emulsion to approximately 70-80 degrees Celsius.

11. The method of claim 10 further comprising cooling the first emulsion and second emulsion to approximately 55-60 degrees Celsius during the step of vibrating the wall of the chamber.

12. The method of claim 11 further comprising the steps of reducing a power of the vibration of the wall;
   cooling the first emulsion and the second emulsion to approximately 47-48 degrees Celsius; and
   adding an additive or flavoring.

13. The method of claim 8 further comprising the step of transferring the vibration of the wall through the fluid, through the first tube face, and into the first cosmetics emulsion.

14. The method of claim 13 further comprising the step of transferring the vibration of the wall through the fluid, through the second tube face, and into the second cosmetics emulsion.

* * * * *